United States Patent
Bagala, Sr.

(10) Patent No.: US 7,045,007 B2
(45) Date of Patent: May 16, 2006

(54) EFFECT PIGMENT

(75) Inventor: Frank Bagala, Sr., Hopewell Junction, NY (US)

(73) Assignee: Engelhard Corporation, Iselin, NJ (US)

( * ) Notice: Subject to any disclaimer, the term of this patent is extended or adjusted under 35 U.S.C. 154(b) by 284 days.

(21) Appl. No.: 10/335,303

(22) Filed: Dec. 31, 2002

(65) Prior Publication Data

US 2004/0123778 A1 Jul. 1, 2004

(51) Int. Cl.
*C04B 14/20* (2006.01)
*C04B 14/22* (2006.01)

(52) U.S. Cl. .................... 106/415; 106/486; 106/417

(58) Field of Classification Search ............. 106/415, 106/417, 486
See application file for complete search history.

(56) References Cited

U.S. PATENT DOCUMENTS

| | | | |
|---|---|---|---|
| 3,087,828 A | 4/1963 | Linton | 106/291 |
| 3,087,829 A | 4/1963 | Linton | 106/291 |
| 4,038,099 A | 7/1977 | DeLuca et al. | 106/291 |
| 4,134,776 A | 1/1979 | Rieger et al. | 106/291 |
| 4,434,010 A | 2/1984 | Ash | 106/291 |
| 5,059,245 A | 10/1991 | Phillips et al. | 106/22 |
| 5,091,011 A | 2/1992 | DeLuca | 106/417 |
| 5,135,812 A | 8/1992 | Phillips et al. | 428/403 |
| 5,156,889 A | 10/1992 | DeLuca | 427/215 |
| 5,277,711 A | 1/1994 | Schmidt et al. | 106/404 |
| 5,281,480 A | 1/1994 | Phillips et al. | 428/412 |
| 5,326,392 A | 7/1994 | Miller et al. | 106/417 |
| 5,423,912 A | 6/1995 | Sullivan et al. | 106/417 |
| 5,433,779 A | 7/1995 | DeLuca | 106/418 |
| 5,753,371 A | 5/1998 | Sullivan et al. | 428/406 |
| 5,759,255 A | 6/1998 | Venturini | 106/418 |
| 5,885,342 A | 3/1999 | Gale et al. | 106/402 |
| 5,958,125 A | 9/1999 | Schmid | 106/417 |
| 6,160,208 A | 12/2000 | Lundquist et al. | 800/320 |
| 6,267,810 B1 * | 7/2001 | Pfaff et al. | 106/415 |
| 6,294,010 B1 * | 9/2001 | Pfaff et al. | 106/415 |
| 6,325,846 B1 | 12/2001 | Bagala et al. | 106/417 |
| 6,334,893 B1 * | 1/2002 | Pfaff et al. | 106/442 |
| 6,440,208 B1 | 8/2002 | Christie et al. | 106/415 |
| 6,471,762 B1 | 10/2002 | DeLuca, Jr. et al. | 106/415 |
| 6,517,628 B1 | 2/2003 | Pfaff et al. | 106/417 |
| 6,533,858 B1 | 3/2003 | Cacace et al. | 106/416 |
| 6,596,070 B1 | 7/2003 | Schmidt et al. | 106/417 |
| 6,632,275 B1 | 10/2003 | Schoen et al. | 106/404 |
| 6,632,276 B1 | 10/2003 | Vogt | 106/417 |
| 6,719,838 B1 * | 4/2004 | Heider et al. | 106/417 |
| 6,743,285 B1 | 6/2004 | Anselmann et al. | 106/415 |
| 2003/0097965 A1 | 5/2003 | Heider et al. | 106/401 |

FOREIGN PATENT DOCUMENTS

| | | |
|---|---|---|
| JP | 8-109341 | 4/1996 |
| WO | WO 02/31059 A2 | 4/2002 |
| WO | WO 02/090448 A2 | 11/2002 |
| WO | WO 03/006558 A2 | 1/2003 |

OTHER PUBLICATIONS

Engelhard's "REFLECKS™ Pearlescent and Iridescent Pigments" re:Effect enhancers for cosmetics and personal care dated 2000.
Engelhard's "Effect enhancers for cosmetics and personal care" price list effective Jul.1, 2001.
In 1999, Engelhard sold a REFLECKS™ Pinpoints of Pearl Pigment.

* cited by examiner

*Primary Examiner*—C. Melissa Koslow
*Assistant Examiner*—Shalie A. Manlove
(74) *Attorney, Agent, or Firm*—Melanie L. Brown

(57) ABSTRACT

An effect pigment is constituted by coated laminar platelets in which the platelets are a mixture of different platelet materials, one of which is platy glass or platy aluminum oxide, and in which the pigment exhibits visual homogeneity.

25 Claims, No Drawings

EFFECT PIGMENT

BACKGROUND OF THE INVENTION

The use of effect pigments, also known as pearlescent pigments or nacreous pigments, in order to impart a pearlescent luster, metallic luster and/or multi-color effect approaching iridescent, is well-known. The effect pigments are composed of a plurality of laminar platelets, each of which is coated with one or more reflecting/transmitting layers. Pigments of this type were first based on metal oxides, as described in U.S. Pat. Nos. 3,087,828 and 3,087,829, and a description of their properties can be found in the *Pigment Handbook*, Volume I, Second Edition, pp. 829–858, John Wiley & Sons, NY 1988. More recently, use of other coating layers to realize optically variable effects have been developed.

The unique appearance of effect pigments is the result of multiple reflections and transmissions of light. The platelet substrate usually has a refractive index which is different from the coating and usually also has a degree of transparency. The coating is in the form of one or more thin films which have been deposited on the surfaces of the platelets.

There are a number of important aspects to effect pigments. One is that they are commonly composed of a plurality of particles which are platelet shaped. If there is a different size or shape, the pearlescent or nacreous appearance is significantly diminished and usually lost to a degree that the material no longer functions as an effect pigment.

One important aspect of the coating on the platelet is that it must be smooth and uniform in order to achieve the optimum pearlescent appearance. The reason is that if an irregular surface is formed, light scattering occurs and the coated platelet will no longer function as an effect pigment.

In addition, the coating should adhere strongly to the platelet or else the coating will become separated during processing, resulting in considerable breakage and loss of luster. Particles which do not become attached to the platelet during preparation of the coatings on the platelets or which are the result of separation cause light scattering and impart opacity to the pigment. When there are too many of such small particles, the pearlescent appearance can be reduced or lost.

The addition of the coatings to a platelet so that the luster, color and color homogeneity are maintained is a very complex process and originally, the only platy substrate which achieved any significant use in commerce was mica. Thus, historically, the largest class of effect pigments based on thin film interference were those based on a mica substrate. With the advent of synthetic substrates, e.g. synthetic mica, aluminum oxide, silica, and glass, it became evident that other substrates could be used since each substrate itself contributes certain effect attributes, due to variations in transparency, refractive index, bulk color, thickness, and surface and edge features. Coated substrate effect pigments thus provide different, albeit similar, visual effects when they are identical except for the identity of the material of the platelet because of these considerations.

Glass flakes are desirable in the industry because they are very resilient and can be optically attractive as well. In one method, glass flakes are made by stretching a molten glass into thin sheets, beads or glass tubes followed by crushing the glass into flakes. The resulting flakes have a size and shape mimicking the mica platelets used in metal oxide-coated mica pearlescent pigments and thus have an average particle size in the range of about 1 to 150 microns and a thickness of about 0.1 to 10 microns.

A commercially viable method of preparing metal oxide-coated glass platelets is described in U.S. Pat. No. 5,753,371, the disclosure of which is hereby incorporated by reference. That patent discloses the coating of C glass in preference to A or E glasses. A glass is a soda-lime glass, commonly used to make windows and contains more sodium than potassium and also contains calcium oxide. C glass, also known as chemical glass, is a form which is resistant to corrosion by acid and moisture. E or electrical glass is, as the name implies, designed for electronic applications and although it is very stable at high temperatures, it can be susceptible to chemical attack.

Metal oxide-coated mica effect pigment and a metal oxide-coated glass effect pigment do provide different visual effects even if they are identical except for the material of the platelet substrate. The reason is that the mica and the glass differ with respect to both their degree of transparency, refractive index, and bulk color. Also, while the surfaces of both are sufficiently smooth for effect pigment use, the glass surface is the smoother of the two substrates and that provides a different optical appearance. Platy aluminum oxide has a surface of similar smoothness to glass. Effect pigments derive their appearance by the reflection and transmission of light and the difference in transparency and refractive index causes the amount of light reflected or transmitted to differ. Nevertheless, both types of effect pigments are highly attractive and commercially valuable.

The preparation of coated glass platelets, while highly desirable, is also expensive. For commercial acceptability, C glass is generally required and this type of glass is costly. In addition, the calcining temperatures employed must be maintained low since the coated glass platelets tend to fuse starting around 650° C. and any significant amount of fusion, generally starting at about 1% by weight of the glass platelets results in the formation of large masses which do not provide the desired pearlescent effect because of their size and irregular shape. Separating the fused platelets from the separate platelets is both time consuming and costly. In addition, the required lower calcining temperature means that the temperature must be maintained for a longer period of time, which also adds to the cost.

Efforts have been made to find a way to reduce the cost of producing the coated glass effect pigment. Theoretically, this could be accomplished by blending coated glass pigment with coated mica pigment. However, this approach has not proven to be effective because the difference in transparency and refractive index between the two platelet materials, in addition to process variations, makes it extremely difficult to match the two blended materials with respect to apparent color. As a practical matter, therefore, it has not been possible to provide a degree of visual homogeneity with a blend which approaches the visual homogeneity of each member of the blend when considered in isolation. This result is not surprising in light of the knowledge in the art. When two or more effect pigments using different substrates are combined together, the attributes of each are present, which results in a unique appearance. One problem with combining effect pigments is that, since the color effects are generated by an additive mechanism instead of a subtractive mechanism, small variations in the color of two effect pigments can result in various degrees of washed out appearance of their blend. This defeats the basic appearance value of the pigment. It can, however, be useful to achieve some other attribute as, for example, to simultaneously achieve an acceptable degree of hiding power and gloss as described in U.S. Pat. No. 6,267,810.

U.S. Pat. No. 5,277,711 describes a mixture of iron oxide-coated aluminum flake and iron oxide-coated mica with or without a prior coating of a colorless, highly refractive metal oxide. The purpose of the iron oxide-coated mica is to reduce the ignition in air and dust explosion hazard otherwise exhibited by the iron oxide-coated aluminum flake. The mixture is made by conjointly coating the aluminum and mica particles with iron oxide in a fluidized bed by gas phase decomposition of iron carbonyls. The appearance of the mixture, homogeneous or otherwise, was not a consideration.

It has now surprisingly been discovered that a visually homogeneous blend of coated effect pigments in which the substrate platelets are of different platy materials can be achieved despite differences in thickness, refractive index and transparency of the platelet materials. It was also surprisingly discovered that with respect to glass platelets premixed with mica, a visually homogeneous product could be made by a process in which the calcining temperature was higher than that employed with coated glass only platelets, thereby reducing the time needed to complete the calcining and further reducing the cost of producing the product.

SUMMARY OF THE INVENTION

This invention relates to an effect pigment which is a mixture of coated platelets of different materials which is visually homogeneous and to the method to produce the effect pigment. More particularly, the effect pigment is a mixture of coated laminar platelets, preferably metal oxide-coated laminar platelets, in which the platelets are a mixture of different materials, e.g., glass and mica, and in which the effect pigment exhibits visual homogeneity which is produced by blending the different platelets before they are coated. The same degree of color homogeneity and appearance is not obtained from a combination of separately coated substrates that are blended after the substrates are coated.

DESCRIPTION OF THE INVENTION

An effect pigment is formed in accordance with the present invention by any process known in the art. It can be accomplished, as one example, by precipitating the metal ion onto laminar platelets and thereafter calcining the coated platelets to provide metal oxide-coated platelets. The metal oxide in most widespread use is titanium dioxide, followed by iron oxide. Other usable oxides include (but are not limited to) tin, chromium and zirconium oxides as well as mixtures and combinations of oxides. For convenience, the description of this process which follows will be primarily concerned with titanium and iron as the metal of the oxide but it will be understood that any other known metal or combination of metals can be used.

In general, the procedure involves dispersing the particulate (flakes) and combining that dispersion with a precursor which results in the formation of a titanium oxide or iron oxide precursor coating on the flakes. Usually, the particulate or flakes are dispersed in water, which is preferably distilled. The average particle size of the flakes preferably used can vary from an average of about 3 microns to an average of about 100 microns, although smaller flakes of down to about 1 micron or less or larger flakes of up to 150 microns or more can also be used if desired. The platelets have a thickness of about 0.1 to 10 µm and an aspect ratio (average particle size/thickness) of at least about 10. The concentration of the particulate in the water can vary from about 5 to 60%, although the generally preferred concentrations vary between about 10 and 20%.

To the water/particulate slurry is added an appropriate metal ion source material. In the case of titanium, titanyl chloride or titanium tetrachloride is preferably used and in the case of iron, the source material is preferably ferric chloride. The pH of the resulting slurry is maintained at an appropriate level during the addition of the titanium or iron salt by the use of a suitable base such as sodium hydroxide in order to cause precipitation of a titanium dioxide or iron oxide precursor on the particulate. Increasing the thickness gives rise to interference colors. If desired, layers of titanium and iron (or other metals) can be deposited sequentially. If necessary to lower the pH, an aqueous acid such as hydrochloric acid can be used. The coated platelets can, if desired, be washed and dried before being calcined to the final effect pigment.

When titanium dioxide-coated products are prepared, both anatase and rutile crystal modifications are possible. The highest quality and most stable pearlescent pigments are obtained when the titanium dioxide is in the rutile form. Some substrates, including both mica and glass, are anatase directing, and it is therefore necessary to modify the foregoing procedure if a rutile product is desired. The modifications necessary to realize a rutile $TiO_2$ are known in the art. One procedure involves the precipitation of a tin oxide entity on the surface of the particulate before the formation of the layer of titanium dioxide precursor. The layered combination is processed and calcined. This procedure is described in detail in U.S. Pat. No. 4,038,099, which is incorporated herein by reference. An alternative procedure is described in U.S. Pat. No. 5,433,779, the disclosure of which is also incorporated by reference, and involves deposition of the titanium dioxide precursor on the substrate in the presence of iron and calcium, magnesium and/or zinc salts without the use of tin. While rutile coatings are preferred, it can be desirable to produce anatase coatings and this is also within the scope of the present invention.

Other coating procedures, such as for example, chemical vapor deposition processes, can also be used.

Optically variable effect pigments have been developed more recently. These are constructed with the substrate being coated with a reflecting layer (e.g., silver, gold, platinum, palladium, rhodium, ruthenium, osmium, iridium or their alloys) which is overcoated with a low index of refraction material, typically having a refractive index from 1.3 to 2.5, that provides a variable path length for light dependent on the angle of incidence of light impinging thereon (for instance, $MgF_2$ or $SiO_2$), which in turn may be overcoated with a third layer selectively transparent to light directed thereon (e.g., silicon, iron oxide, chromium oxide, a mixed metal oxide, titanium dioxide, titanium nitride and aluminum, as well as the same materials as the first layer provided they are sufficiently thin as to be selectively transparent). Examples of such pigments and the processes by which they can be produced can be found, inter alia, in U.S. Pat. Nos. 5,135,812, 4,434,010, 5,059,245, 5,281,480, 5,958,125, 6,160,208, 6,325,847 and 6,440,208, the disclosure of which is also incorporated by reference.

The coated substrates, however produced, can be post-treated by any procedure known in the art. Examples of such treatments can for instance be found in U.S. Pat. Nos. 4,134,776, 5,091,011, 5,156,889, 5,326,392, 5,423,912, 5,759,255, and 6,325,846, which are hereby incorporated herein by reference, but are not limited to those procedures.

The laminar substrates employed in the present invention are a blend of two or more laminar substrates. One of the substrates is either platy aluminum oxide or platy glass. The other laminar substrate can be the other of the platy aluminum oxide or platy glass, or can be any other platy material such as aluminum, mica, bismuth oxychloride, platy iron oxide, platy graphite, platy silica, and the like. For convenience, the following description will focus on the combination of glass and mica, although other combinations can be used. Mica is desirable because of its high transparency, strong reflectance and strong chroma, primarily due to the presence of small, coated flakes. Glass flakes have the attributes of high transparency, very white bulk color and a sparkle effect in strong light but, as noted above, its high cost and melting point preclude its use in many applications.

Individually, each substrate can constitute about 5 to 90% of the mixture although it is preferred that the majority of the blend is constituted by one substrate, e.g., mica. More preferably, the blend contains at least about 65% mica and even more preferably at least about 75% mica. Individually, the mica platelets and glass platelets have an average particle size and thickness in the ranges specified above. The particle dimensions are selected so that the resulting coated product exhibits visual homogeneity, i.e., exhibits an increase relative to a blend of the same proportion of the substrates of at least 5 chroma units (CieLab) when evaluated with an X-Rite MA 68 at 25° from the specular angle. Preferably, the increase is at least 10 chroma units (CieLab) and to achieve that result, the average particle size of the smaller of the glass and mica platelets are preferably within about 25% of the size of the larger of the glass and mica platelets. While it is preferable to employ C glass, as in the prior art, any type of glass can be used in the present invention.

The substrate coating procedure employed is adjusted such that the two or more substrate materials coat at substantially the same rate to thereby develop a coating of similar quality and thickness. This may involve control of the temperature, reagent addition rate, reagent identity, substrate pretreatment, and the like. Frequently, this control is more easily achieved as the platelets become closer to each other in average size and thickness. The modifications necessary or appropriate can easily be established by those of skill in this art with a few preliminary runs to establish the appropriate parameters.

The procedure described above in which the glass and mica platelets are blended before being coated unexpectedly results in a product which exhibits visual homogeneity, showing a uniform color, which cannot be achieved by forming a blend of previously prepared coated mica and coated glass platelets. This result is achieved despite the fact that the mica and glass substrates have different degrees of transparency and refractive index and, usually, have a different thickness.

The calcining of coated glass flakes is typically done in the neighborhood of 600° C. because the glass platelets fuse at about 650–700° C. creating a mass having greatly diminished quality. Surprisingly, it has been found that a blend of glass and mica, coated with a metal oxide precursor, is capable of being calcined at temperatures of 650° C. up to about 850° C. without causing the glass flakes to fuse. Preferably, the calcining temperature is about 675 to 825° C. and most preferably, about 800° C. when the metal oxide is $TiO_2$ and about 700° C. when the metal oxide is $Fe_2O_3$.

The resulting pigment can be used in any application for which effect pigments have been used heretofore such as, for instance, in cosmetics, plastics, inks and coatings including solvent and water borne automotive paint systems. Products of this invention have an unlimited use in all types of automotive and industrial paint applications, especially in the organic color coating and inks field where deep color intensity is required. For example, these pigments can be used in mass tone or as styling agents to spray paint all types of automotive and non-automotive vehicles. Similarly, they can be used on all clay/formica/wood/ glass/metal/enamel/ ceramic and non-porous or porous surfaces. The pigments can be used in powder coating compositions. They can be incorporated into plastic articles geared for the toy industry or the home. These pigments can be impregnated into fibers to impart new and esthetic coloring to clothes and carpeting. They can be used to improve the look of shoes, rubber and vinyl/marble flooring, vinyl siding, and all other vinyl products. In addition, these colors can be used in all types of modeling hobbies.

The above-mentioned compositions in which the compositions of this invention are useful are well known to those of ordinary skill in the art. Examples include printing inks, nail enamels, lacquers, thermoplastic and thermosetting materials, natural resins and synthetic resins. Some non-limiting examples include polystyrene and its mixed polymers, polyolefins, in particular, polyethylene and polypropylene, polyacrylic compounds, polyvinyl compounds, for example polyvinyl chloride and polyvinyl acetate, polyesters and rubber, and also filaments made of viscose and cellulose ethers, cellulose esters, polyamides, polyurethanes, polyesters, for example polyglycol terephthalates, and polyacrylonitrile.

For a well-rounded introduction to a variety of pigment applications, see Temple C. Patton, editor, The Pigment Handbook, volume II, Applications and Markets, John Wiley and Sons, New York (1973). In addition, see for example, with regard to ink: R. H. Leach, editor, The Printing Ink Manual, Fourth Edition, Van Nostrand Reinhold (International) Co. Ltd., London (1988), particularly pages 282–591; with regard to paints: C. H. Hare, Protective Coatings, Technology Publishing Co., Pittsburgh (1994), particularly pages 63–288. The foregoing references are hereby incorporated by reference herein for their teachings of ink, paint and plastic compositions, formulations and vehicles in which the compositions of this invention may be used including amounts of colorants. For example, the pigment may be used at a level of 10 to 15% in an offset lithographic ink, with the remainder being a vehicle containing gelled and ungelled hydrocarbon resins, alkyd resins, wax compounds and aliphatic solvent. The pigment may also be used, for example, at a level of 1 to 10% in an automotive paint formulation along with other pigments which may include titanium dioxide, acrylic lattices, coalescing agents, water or solvents. The pigment may also be used, for example, at a level of 20 to 30% in a plastic color concentrate in polyethylene.

In the cosmetic field, these pigments can be used in the eye area and in all external and rinse-off applications. Thus, they can be used in hair sprays, face powder, leg-makeup, insect repellent lotion, mascara cake/cream, nail enamel, nail enamel remover, perfume lotion, and shampoos of all types (gel or liquid). In addition, they can be used in shaving cream (concentrate for aerosol, brushless, lathering), skin glosser stick, skin makeup, hair groom, eye shadow (liquid, pomade, powder, stick, pressed or cream), eye liner, cologne stick, cologne, cologne emollient, bubble bath, body lotion (moisturizing, cleansing, analgesic, astringent), after shave lotion, after bath milk and sunscreen lotion.

For a review of cosmetic applications, see Cosmetics: Science and Technology, 2nd Ed., Eds: M. S. Balsam and Edward Sagarin, Wiley-Interscience (1972) and deNavarre, The Chemistry and Science of Cosmetics, 2nd Ed., Vols 1 and 2 (1962), Van Nostrand Co. Inc., Vols 3 and 4 (1975), Continental Press, both of which are hereby incorporated by reference.

In order to further illustrate the invention, various non-limiting examples will be set forth below. In these examples, as well as throughout the balance of this specification and claims, all parts and percentages are by weight and all temperatures are in degrees Centigrade unless otherwise indicated.

EXAMPLES 1–4

A blend of 50 grams of C glass flakes having an average particle size of about 140 microns (by laser light scattering) were mixed with 50 grams of muscovite mica having an average particle size of about 80 microns. The mixture was dispersed in 750 ml of water and iron and zinc were introduced in the form of 1 ml of a 39% aqueous solution of ferric chloride and 7 ml of a 9% aqueous zinc chloride solution. The pH of the slurry was adjusted to 3.0 using a 35% aqueous sodium hydroxide solution and the slurry was heated to a temperature of 76° C. The pH was then lowered to 1.6 by the addition of hydrochloric acid and a 40% aqueous solution of titanium tetrachloride was added at a rate of 100 ml/hour while the pH was maintained at 1.6 by the addition of 35% aqueous sodium hydroxide. The titanium introduction was continued until an appearance of either a white pearl or the interference colors gold, red and blue had been reached. When the desired endpoint was achieved, the slurry was filtered on a Buchner funnel and washed with additional water. The coated platelets were then dried and calcined at about 800° C.

Microscopic evaluation of the resulting pigments shows the platelets are coated with a smooth homogeneous layer of titanium dioxide. The coated pigments were visually homogeneous.

The luster and color of the resulting pigments were evaluated visually and instrumentally using drawdowns on a hiding chart (Form 2–6 opacity charts of The Leneta Company), half of which is black and half of which is white. A coating on the black part of this chart displays the reflection color and luster when it is examined specularly, while the coating on the white portion displays the transmission color when it is viewed at non-specular angles. Drawdowns are prepared by incorporating pigment at a 12% concentration in a nitrocellulose lacquer and applying the suspension to the black and white chart with a Bird film applicator bar. The drawdowns prepared in these examples show a series of vibrant, high-quality colors with high chromaticity and coverage.

EXAMPLES 5–9

100 grams of the glass/mica blend of Examples 1–4 were dispersed in 330 ml of distilled water which was then heated to 74° C. and the pH adjusted to 1.6 using dilute hydrochloric acid. Then 7 ml of an 18% aqueous stannous chloride solution was slowly added followed by a 40% aqueous solution of titanium tetrachloride at a rate of 100 ml/hour. The pH was maintained at 1.6 during the addition of the tin and titanium by simultaneously adding a dilute aqueous solution of sodium hydroxide. The titania addition was continued until either a white pearl or the interference color gold, red, blue or green was observed. When the desired endpoint was reached, the slurry was filtered and washed with additional water and calcined at 800° C.

Microscopic evaluation of the resulting pigments shows the platelets are coated with a smooth homogeneous layer of titanium dioxide. The coated pigments were visually homogeneous.

Drawdowns prepared in the pigments of these examples show a series of vibrant, high-quality colors with high chromaticity and coverage.

EXAMPLES 10–17

75 grams of the glass/mica blend of Examples 1–4 were dispersed in 300 ml of distilled water. The dispersion was heated to 76° C. and the pH adjusted to 3.2 with dilute hydrochloric acid. An aqueous ferric chloride solution was added to the suspension at 0.2 ml/min. while maintaining the pH at 3.2 using dilute sodium hydroxide. The ferric chloride addition continued until a desired color was observed, at which point the slurry was filtered, washed with water and calcined at 800° C. to yield a ferric oxide coated effect pigment.

Since ferric oxide has an inherent red color, flakes coated with this oxide have both a reflection color and an absorption color. The interference color is from interference of light, while the absorption color is due to the absorption of light. The reflection color changes from gold to red to blue to green as increasing amounts of iron (III) oxide are coated on the laminar flakes. As even more iron (III) oxide is added, thicker coatings of the $Fe_2O_3$ are obtained which yield another series of interference colors known as second observable interference colors. The second colors have even higher color intensity than the first colors. If the coating process is continued even further, a third series of interference colors can be obtained.

When the iron oxide-coated flakes were drawndown, a series of vivid, high quality colors are observed. The interference colors realized in these examples were bronze, first orange, first red, first violet-blue, first green, second orange, second red, and second green.

EXAMPLES 18–20

Titanium dioxide can produce a series of interference colors as the thickness of the titanium dioxide layer increases. It produces a whitish reflection which appears pearly or silver initially, and as the $TiO_2$ layer becomes thicker, gold, red, blue and green interference colors are observed. As the coating becomes even thicker, a series of second observable color is observed. The second colors have more color intensity than the first colors described in the Examples above.

The second colors were prepared by dispersing 50 grams of the mica/glass blend used in Examples 1–4 in 333 ml of distilled water. The pH was adjusted to 1.6 with dilute hydrochloric acid and the suspension heated to 74° C. Then 7 ml of an 18% stannous chloride solution was added followed by the addition of 40% titanium chloride at a rate of 0.33 ml/min. The pH was maintained at 1.6 by simultaneously adding dilute sodium hydroxide. The titanium addition continued until the desired color was achieved, at which point the slurry was filtered, washed with water and calcined at 800° C. In this manner, the second colors gold, orange and red are achieved. When drawndown, the products had higher color intensity than their comparable first observable interference colors.

EXAMPLES 21–25

The procedure of Examples 5–9 was repeated except that the laminar platelet blend was constituted by 75 parts of muscovite mica having an average particle size of about 25 microns and 25 parts of C glass flakes having an average particle size of about 25 microns

EXAMPLES 26–33

The procedure of Examples 10–17 was repeated except that the laminar platelet blend was constituted by 75 parts of muscovite mica having an average particle size of about 25 microns and 25 parts of C glass flakes having an average particle size of about 25 microns.

EXAMPLE 34–41

The procedure of Examples 10–17 was repeated except that the laminar platelet blend was constituted by a blend of 50 grams of platy aluminum oxide having an average particle size of about 20 microns (by laser light scattering) and 50 grams of muscovite mica having an average particle size of about 25 microns.

EXAMPLE 42

A blend of 150 grams of muscovite mica having an average particle size of approximately 25 µm, were mixed with 50 grams of glass flake with of nominal thickness of 1 µm and a major dimension ($D_{50}$) of 20 µm. The mixture was dispersed in 2,000 ml of distilled water and heated to 78° C. At that temperature, the pH of the slurry was reduced to 1.5 with dilute HCl solution and 20 grams of a 18% $SnCl_4$ solution were added at 0.4 ml/min while maintaining the pH at 1.5 with the NaOH solution. Following the addition of the $SnCl_4$ solution, the pH was raised to 3.2 with dilute NaOH and 39% $FeCl_3$ was added at 1.5 ml/min, until the desired color was achieved The product was then washed, dried and heat treated at 650° C.

EXAMPLE 43

The product of Example 42 was dispersed in a commercial automotive urethane refinish paint formulation and evaluated with an X-Rite MA 68 for chroma at 25° and 15° from the specular angle. Values obtained from the sample where the substrates had been preblended prior to coating and from a sample prepared in a similar fashion with the same proportions of individually coated substrates are set forth in the tables below. The preblended sample showed an increase in chroma of over 10 units (CieLab) at each angle, namely 76.1 vs. 59.7 at 15° and 62.4 vs.51.8 at 25°.

|  | L | a | b | C |
|---|---|---|---|---|
| 15° from Specular | | | | |
| Example 42 | 76.8 | 64.4 | 40.5 | 76.1 |
| Blend | 80.0 | 56.5 | 19.1 | 59.7 |
| 25° from Specular | | | | |
| Example 42 | 56.4 | 61.7 | 33.5 | 62.4 |
| Blend | 52.6 | 48.5 | 18.3 | 51.8 |

EXAMPLE 44

A blend of 50 grams of platy aluminum oxide having an average particle size of about 20 microns (by laser light scattering) is mixed with 50 grams of muscovite mica having an average particle size of about 25 microns. The mixture is dispersed in 750 ml of water and iron and zinc are introduced in the form of 1 ml of a 39% aqueous solution of ferric chloride and 7 ml of a 9% aqueous zinc chloride solution. The pH of the slurry is adjusted to 3.0 using a 35% aqueous sodium hydroxide solution and the slurry is heated to a temperature of 76° C. The pH is then lowered to 1.6 by the addition of hydrochloric acid and a 40% aqueous solution of titanium tetrachloride added at a rate of 100 ml/hour while the pH is maintained at 1.6 by the addition of 35% aqueous sodium hydroxide. The titanium introduction is continued until an appearance of a white pearl had been reached. When the desired endpoint is achieved, the slurry is filtered on a Buchner funnel and washed with additional water. The coated platelets are then dried and calcined at about 800° C.

EXAMPLE 45

One hundred grams of an equal weight mixture of glass flakes (100 µ average major dimension) and mica (100 µ average major dimension) is placed in a 1 liter beaker equipped with a magnetic stir bar and containing 393 grams of a 2% dextrose solution. The slurry is stirred at room temperature. A solution, containing 7.87 grams of silver nitrate crystals, 375 ml distilled water and enough 29% ammonium hydroxide solution to dissolve any precipitate, is rapidly added to the slurry. The supernatant liquid is tested for silver ion by the addition of a few drops of concentrated hydrochloric acid. The test is a visual assessment of any precipitate and/or turbidity and when none is found, the slurry is filtered and rinsed several times with distilled water and the presscake is dried at 100° C. to a constant mass. The dried sample is a lustrous, opaque and silver colored material.

50 grams of the silver-coated material is slurried into 600 ml of isopropanol at 25° C. To the slurry is added 75 grams of distilled water, 3.5 grams of 29% $NH_4OH$ and 75 grams of tetraethoxysilane. The slurry is stirred for 7 hours at room temperature and then filtered, and the product washed and oven dried.

10 grams of this silica-coated material is slurried into 50 grams of 1% dextrose solution. A solution of 0.4 grams of $AgNO_3$, 40 grams of water and a slight excess of 29% ammonium hydroxide solution is quickly added to the slurry. When the slurry supernatant liquid tests negative for silver ion, it is filtered and the product washed and dried at 120° C. The product displays a very clean color flop from blue to violet upon a change in viewing angle of a lacquer film containing the product, and the pigment is visually homogeneous.

EXAMPLE 46

The pigment of Example 1 can be formulated into a powder eye shadow as follows:

The following materials are thoroughly blended and dispersed:

| Ingredients | wt parts |
|---|---|
| Mearltalc TCA ® (Talc) | 18 |
| Mearlmica ® SVA (Mica) | 20 |
| Magnesium Myristate | 5 |
| Silica | 2 |
| Cloisonne ® Red 424C (red $TiO_2$-coated mica) | 20 |
| Cloisonne ® Violet 525C (violet $TiO_2$-coated mica) | 13 |
| Cloisonne ® Nu-Antique Blue 626CB ($TiO_2$-coated mica/iron oxide-coated mica) | 2 |
| Cloisonne ® Cerise Flambe 550Z (iron oxide-coated mica) | 2 |
| Preservatives & Antioxidant | q.s. |

Then 7 parts of octyl palmitate and 1 part of isostearyl neopentanoate are heated and mixed until uniform, at which time the resulting mixture is sprayed into the dispersion and the blending continued. The blended material is pulverized and then 5 parts of Cloisonne Red 424C and 5 parts of the pigment of example 1 added and mixed until a uniform powder eye shadow is obtained.

EXAMPLE 47

The pigment of Example 1 can be formulated into a lipstick as follows.

The following amounts of the listed ingredients are placed into a heated vessel and the temperature raised to 85±3° C.

|  | wt parts |
| --- | --- |
| Candelilla Wax | 2.75 |
| Carnauba Wax | 1.25 |
| Beeswax | 1.00 |
| Ceresine Wax | 5.90 |
| Ozokerite Wax | 6.75 |
| Microcrystalline Wax | 1.40 |
| Oleyl Alcohol | 3.00 |
| Isostearyl Palmitate | 7.50 |
| Isostearyl Isostearate | 5.00 |
| Caprylic/Capric Triglyceride | 5.00 |
| Bis-Diglycerylpolyalcohol Adipate | 2.00 |
| Acetylated Lanolin Alcohol | 2.50 |
| Sorbitan Tristearate | 2.00 |
| Aloe Vera | 1.00 |
| Castor Oil | 37.50 |
| Red 6 Lake | 0.25 |
| Tocopheryl Acetate | 0.20 |
| Phenoxyethanol, isopropylparaben, and burylparaben | 1.00 |
| Antioxidant | q.s. |

Then, 14 parts of the pigment of Example 1 are added and mixed until all of the pigment is well dispersed. Fragrance is added as desired and mixed with stirring. The resulting mixture is poured into molds at 75±5° C., allowed to cool and flamed into lipsticks.

Various changes and modifications can be made in the products and process of the present invention without departing from the spirit and scope thereof. The various embodiments which have been disclosed herein were for the purpose of further illustrating the invention but were not intended to limit it.

What is claimed is:

1. An effect pigment comprising metal oxide-coated laminar platelets in which the platelets are a mixture of about 5 to 90% platy glass and 90 to 5% platy mica and in which the effect pigment exhibits visual homogeneity.

2. An effect pigment according to claim 1 wherein the mica is a majority of the platelet mixture.

3. An effect pigment according to claim 1, wherein the mica is at least about 65% of the platelet mixture.

4. An effect pigment according to claim 1, wherein the mica is at least about 75% of the platelet mixture.

5. An effect pigment according to claim 1, wherein the metal oxide comprises iron oxide.

6. An effect pigment according to claim 1, wherein the metal oxide comprises titanium dioxide.

7. An effect pigment according to claim 6, wherein the metal oxide is rutile titanium dioxide.

8. An effect pigment according to claim 1, wherein the metal oxide coating comprises a plurality of layers, each of which comprises a metal oxide.

9. In a coating composition comprising a pigment and a carrier, the pigment comprising an effect pigment according to claim 1.

10. In a plastic composition comprising a pigment and a carrier, the pigment comprising an effect pigment according to claim 1.

11. In a cosmetic composition comprising a pigment and a carrier, the pigment comprising an effect pigment according to claim 1.

12. In an ink composition comprising a pigment and a carrier, the pigment comprising an effect pigment according to claim 1.

13. A method of producing an effect pigment comprising coating a blend of laminar platelets comprising a mixture of different materials, wherein one of the different platelet materials is platy glass or aluminum oxide.

14. A method of producing an effect pigment according to claim 13, wherein the platelets are coated with metal oxide precursor and the resulting metal oxide precursor-coated platelets are calcined.

15. A method of producing an effect pigment according to claim 14, wherein said mixture comprises about 5 to 90% glass and about 90 to 5% mica.

16. A method of producing an effect pigment according to claim 15, wherein the mica is a majority of the platelet mixture.

17. A method of producing an effect pigment according to claim 16, wherein the mica is at least about 65% of the platelet mixture.

18. A method of producing an effect pigment according to claim 17, wherein the mica is at least about 75% of the platelet mixture.

19. A method of producing an effect pigment according to claim 18, wherein the metal oxide precursor comprises titanium dioxide or iron oxide precursor.

20. A method of producing an effect pigment according to claim 13, wherein the laminar platelets are coated with a plurality of metal oxide layers.

21. A method of producing an effect pigment according to claim 14, wherein the laminar platelets are coated with metal oxide to an interference thickness.

22. A method of producing an effect pigment according to claim 14, wherein the laminar platelets are calcined at a temperature in the range of about 650 to 850° C.

23. An effect pigment produced by the method of claim 18.

24. An effect pigment produced by the method of claim 15.

25. An effect pigment produced by the method of claim 13.

* * * * *